United States Patent
Kozloski et al.

(10) Patent No.: US 10,265,001 B2
(45) Date of Patent: *Apr. 23, 2019

(54) MOUTHGUARD FOR ANALYSIS OF BIOMARKERS FOR TRAUMATIC BRAIN INJURY

(71) Applicant: INTERNATIONAL BUSINESS MACHINES CORPORATION, Armonk, NY (US)

(72) Inventors: James R. Kozloski, New Fairfield, CT (US); Mark C. H. Lamorey, Williston, VT (US); Clifford A. Pickover, Yorktown Heights, NY (US); John J. Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 25 days.

This patent is subject to a terminal disclaimer.

(21) Appl. No.: 14/745,494

(22) Filed: Jun. 22, 2015

(65) Prior Publication Data

US 2016/0331296 A1    Nov. 17, 2016

Related U.S. Application Data

(63) Continuation of application No. 14/709,570, filed on May 12, 2015.

(51) Int. Cl.
*A61B 5/145*    (2006.01)
*A61B 5/00*    (2006.01)
(Continued)

(52) U.S. Cl.
CPC .......... *A61B 5/14546* (2013.01); *A42B 3/046* (2013.01); *A61B 5/0002* (2013.01);
(Continued)

(58) Field of Classification Search
CPC . A61B 5/145; A61B 5/14507; A61B 5/14546; A61B 5/68; A61B 5/6803;
(Continued)

(56) References Cited

U.S. PATENT DOCUMENTS 7,396,654 B2 *   7/2008   Hayes ................ G01N 33/6896
                                                                   435/4
8,126,731 B2 *   2/2012   Dicks .................. G06F 19/3418
                                                                   705/2

(Continued)

OTHER PUBLICATIONS

List of IBM Patents or Patent Applications Treated as Related—Date Filed: Aug. 6, 2015; 2 pages.
(Continued)

*Primary Examiner* — Eric F Winakur
(74) *Attorney, Agent, or Firm* — Cantor Colburn LLP; Vazken Alexanian (57) ABSTRACT

Embodiments include methods, systems and computer program products for monitoring a user of a helmet for traumatic brain injury. Aspects include obtaining a saliva specimen from a mouthguard and providing the saliva specimen to a lab on chip. Aspects further include determining whether the saliva specimen contains a biomarker that indicates the user suffered a traumatic brain injury and creating an alert that the user of the helmet has suffered a traumatic brain injury.

6 Claims, 6 Drawing Sheets

(51) Int. Cl.
  *A61B 10/00* (2006.01)
  *G06F 19/00* (2018.01)
  *A42B 3/04* (2006.01)
  *G16H 40/63* (2018.01)
  *G16H 50/20* (2018.01)

(52) U.S. Cl.
  CPC ............ *A61B 5/4064* (2013.01); *A61B 5/682* (2013.01); *A61B 5/6803* (2013.01); *A61B 5/7275* (2013.01); *A61B 5/746* (2013.01); *A61B 10/0051* (2013.01); *G06F 19/00* (2013.01); *G16H 40/63* (2018.01); *G16H 50/20* (2018.01); *A61B 2562/0219* (2013.01)

(58) Field of Classification Search
  CPC ..... A61B 5/6813; A61B 5/682; A61B 5/6895; A61B 5/72; A63B 71/085
  See application file for complete search history.

(56) References Cited

U.S. PATENT DOCUMENTS

| | | | | |
|---|---|---|---|---|
| 2004/0220498 | A1* | 11/2004 | Li | A61B 5/145 600/309 |
| 2009/0221884 | A1* | 9/2009 | Ryan | A61B 5/682 600/301 |
| 2013/0066236 | A1* | 3/2013 | Herman | A63B 71/085 600/595 |
| 2014/0379369 | A1* | 12/2014 | Kokovidis | A61B 5/002 705/2 |
| 2016/0178643 | A1* | 6/2016 | Everett | G01N 33/6893 435/7.92 |

OTHER PUBLICATIONS

U.S. Appl. No. 14/664,987, filed Mar. 23, 2015; Entitled: Monitoring a Person for Indications of a Brain Injury.
U.S. Appl. No. 14/664,989, filed Mar. 23, 2015; Entitled: Monitoring a Person for Indications of a Brain Injury.
U.S. Appl. No. 14/664,991, filed Mar. 23, 2015; Entitled: Monitoring a Person for Indications of a Brain Injury.
U.S. Appl. No. 14/709,563, filed May 12, 2015; Entitled: "Helmet Having a Cumulative Concussion Indicator".
U.S. Appl. No. 14/709,564, filed May 12, 2015; Entitled: "Monitoring Impacts Between Individuals for Concussion Analysis".
U.S. Appl. No. 14/709,568, filed May 12, 2015; Entitled: "Helmet Having an Embedded Cooling Array".
U.S. Appl. No. 14/709,570, filed May 12, 2015; Entitled: "Mouthguard for Analysis of Biomarkers for Traumatic Brain Injury".
U.S. Appl. No. 14/709,572, filed May 12, 2015; Entitled: "Suggesting Adjustments to a Helmet Based on Analysis of Play".
U.S. Appl. No. 14/709,574, filed May 12, 2015; Entitled: "Automatic Adjustment of Helmet Parameters Based on a Category of Play".
U.S. Appl. No. 14/709,575, filed May 12, 2015; Entitled: "Detection of a Traumatic Brain Injury with a Mobile Device".
U.S. Appl. No. 14/744,061, filed Jun. 19, 2015; Entitled: Monitoring a Person for Indications of a Brain Injury.
U.S. Appl. No. 14/744,063, filed Jun. 19, 2015; Entitled: Monitoring a Person for Indications of a Brain Injury.
U.S. Appl. No. 14/744,064, filed Jun. 19, 2015; Entitled: Monitoring a Person for Indications of a Brain Injury.
U.S. Appl. No. 14/745,491, filed Jun. 22, 2015; Entitled: "Automatic Adjustment of Helmet Parameters Based on a Category of Play".
U.S. Appl. No. 14/745,492, filed Jun. 22, 2015; Entitled: "Detection of a Traumatic Brain Injury with a Mobile Device".
U.S. Appl. No. 14/745,493, filed Jun. 22, 2015; Entitled: "Suggesting Adjustments to a Helmet Based on Analysis of Play".
U.S. Appl. No. 14/745,495, filed Jun. 22, 2015; Entitled: "Helmet Having an Embedded Cooling Array".
U.S. Appl. No. 14/745,497, filed Jun. 22, 2015; Entitled: "Monitoring Impacts Between Individuals for Concussion Analysis".
U.S. Appl. No. 14/745,498, filed Jun. 22, 2015; Entitled: "Helmet Having a Cumulative Concussion Indicator".

* cited by examiner

MOUTHGUARD FOR ANALYSIS OF BIOMARKERS FOR TRAUMATIC BRAIN INJURY

DOMESTIC PRIORITY

This application is a continuation of U.S. application Ser. No. 14/709,570; Filed: May 12, 2015; which is related to U.S. application Ser. No. 14/709,575; Filed: May 12, 2015; application Ser. No. 14/709,574; Filed May 12, 2015; U.S. application Ser. No. 14/709,572; Filed: May 12, 2015; U.S. application Ser. No. 14/709,563; Filed: May 12, 2015; U.S. application Ser. No. 14/709,568; Filed: May 12, 2015; U.S. application Ser. No. 14/709,564; Filed: May 12, 2015; U.S. application Ser. No. 14/664,987; Filed Mar. 23, 2015; U.S. application Ser. No. 14/664,989; Filed: Mar. 23, 2015; and U.S. application Ser. No. 14/664,991; Filed: Mar. 23, 2015; the contents of each of which are herein incorporated by reference in their entirety.

BACKGROUND

The present disclosure relates to monitoring an individual for a traumatic brain injury, and more specifically, to methods, systems and computer program products for using a mouthguard to analyze biomarkers in saliva to monitor a person for a traumatic brain injury.

Generally speaking, safety is a primary concern for both users of helmets and manufacturers of helmets. Helmets are used by individuals that participate in activities that have risk of head trauma, such as the area of sports, biking, motorcycling, etc. While helmets have traditionally been used to provide protection from blunt force trauma to the head, an increased awareness of concussion causing forces has motivated a need for advances in helmet technology to provide increased protection against concussions. A concussion is a type of traumatic brain injury that is caused by a blow to the head that shakes the brain inside the skull due to linear or rotational accelerations. Recently, research has linked concussions to a range of health problems, from depression to Alzheimer's, along with a range of brain injuries. Unlike severe traumatic brain injuries, which result in lesions or bleeding inside the brain and are detectable using standard medical imaging, a concussion is often invisible in brain tissue, and therefore only detectable by means of a cognitive change, where that change is measurable by changes to brain tissue actions, either neurophysiological or through muscle actions caused by the brain and the muscles resulting effects on the environment, for example, speech sounds.

Currently available helmets use accelerometers to measure the forces that the helmet, and therefore the head of the user, experiences. These accelerometers can be used to indicate when a force experienced by a helmet may be sufficiently large so as to pose a risk of a concussion to the user. However, currently available helmets are prone to providing false positives which can lead to unnecessary downtime for the user of the helmet. In addition, a large number of false positives may lead to individuals disregarding the indications generated and therefore a further degradation of the effectiveness of the monitoring.

SUMMARY

In accordance with an embodiment, a method for monitoring an individual for a traumatic brain injury includes obtaining a saliva specimen from a mouthguard and providing the saliva specimen to a lab on chip. The method also includes determining whether the saliva specimen contains a biomarker that indicates the user suffered a traumatic brain injury and creating an alert that the user of the helmet has suffered a traumatic brain injury.

In accordance with another embodiment, a system for monitoring a user for traumatic brain injury includes a lab on chip configured to receive a saliva specimen from a mouthguard and to determine whether the saliva specimen contains a biomarker that indicates the user suffered a traumatic brain injury. The system also includes a processor configured to communicate with the lab on chip, wherein the processor creates an alert that the user of the helmet has suffered the traumatic brain injury in response to the lab on chip determining that the saliva sample contains the biomarker.

In accordance with a further embodiment, a computer program product for monitoring an individual for a traumatic brain injury includes a non-transitory storage medium readable by a processing circuit and storing instructions for execution by the processing circuit for performing a method. The method includes obtaining a saliva specimen from a mouthguard and providing the saliva specimen to a lab on chip. The method also includes determining whether the saliva specimen contains a biomarker that indicates the user suffered a traumatic brain injury and creating an alert that the user of the helmet has suffered a traumatic brain injury.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In accordance with exemplary embodiments of the disclosure, methods, systems and computer program products for monitoring an individual for a traumatic brain injury are provided. In exemplary embodiments, individuals involved in activities that may result in traumatic brain injury wear a helmet and a mouthguard that is in communication with the helmet. The mouthguard is configured to collect saliva that is analyzed for biomarkers in the saliva of the user. In exemplary embodiments, the saliva is analyzed using lab on chip technology that can be disposed in the mouthguard or in the helmet. Upon detection of a biomarker that may indicate that the user has suffered a traumatic brain injury, an alert is created.

In exemplary embodiments, the helmet may include one or more such as accelerometers, gyroscopes, or the like. In general, the outputs of the sensors are used by the processor of the helmet to monitor impacts suffered by the user. In exemplary embodiments, the severity of the impact may include the amount of acceleration and or rotation experienced by the helmet. The processor may use data from the mouthguard and from the sensors to determine the likelihood that a user has suffered a traumatic brain injury.

Figure 1:
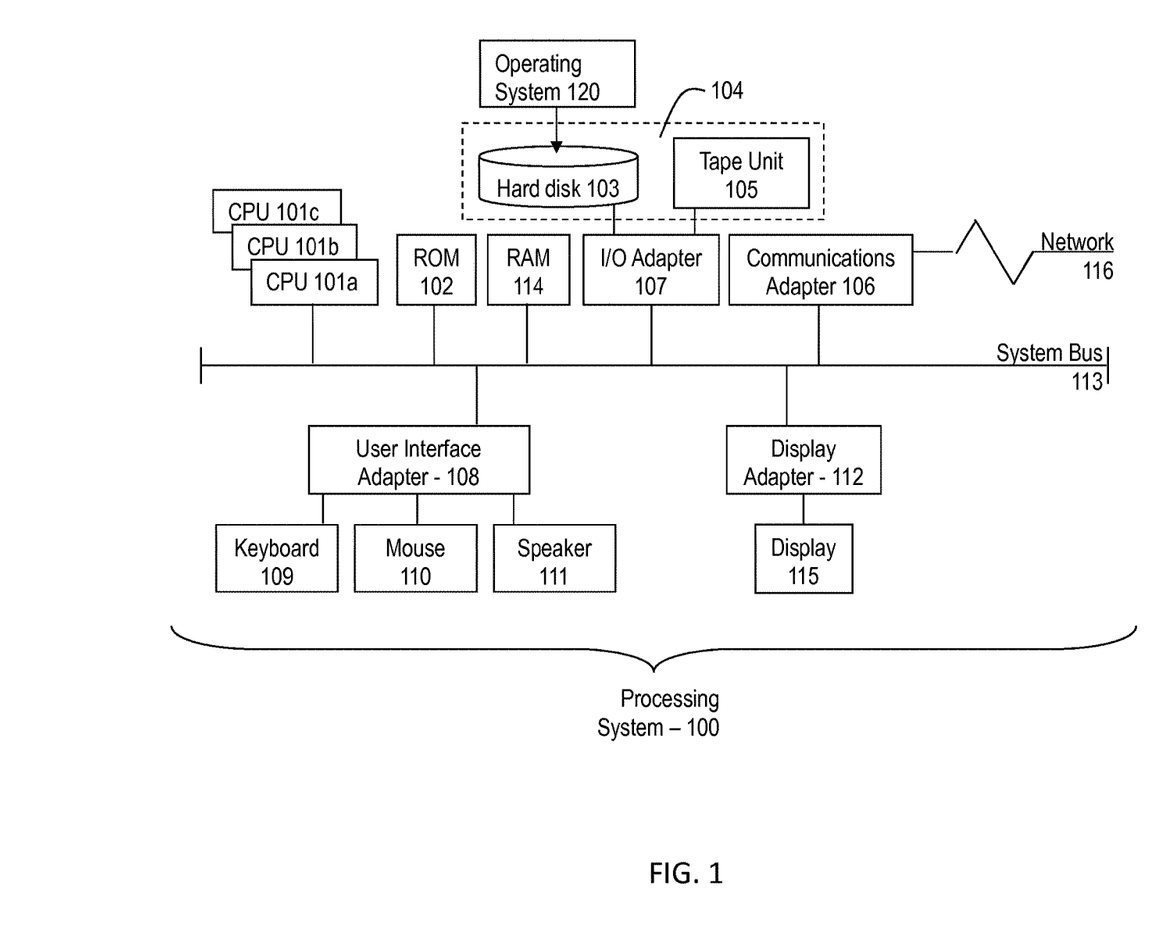
FIG. 1 is a block diagram illustrating one example of a processing system for practice of the teachings herein.

Referring now to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
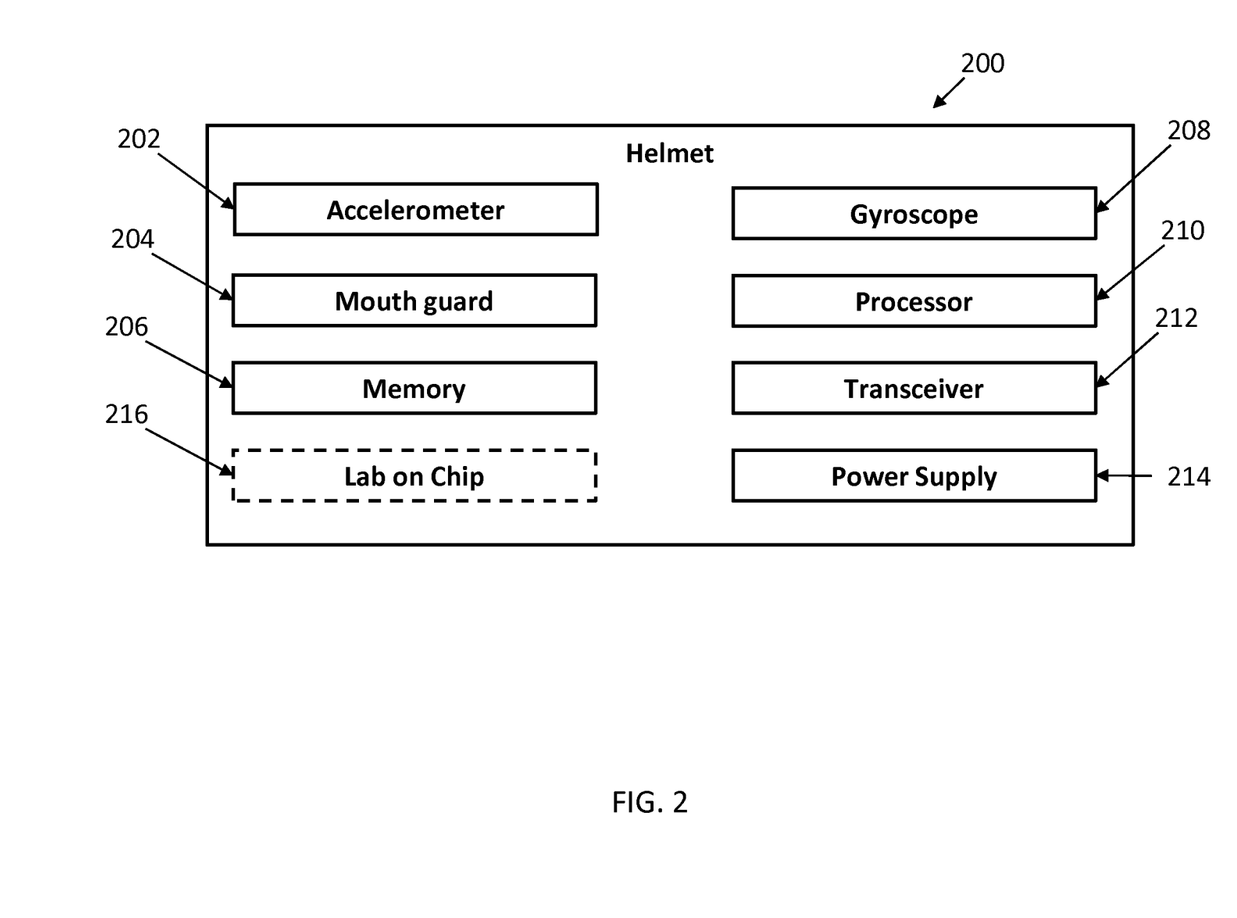
FIG. 2 is a block diagram illustrating a helmet in accordance with an exemplary embodiment.

Referring to FIG. 2, a block diagram illustrating a helmet 200 in accordance with an exemplary embodiment is shown. The term "helmet" may include, but is not intended to be limited to, a football helmet, a motorcycle helmet or the like. In exemplary embodiments, the helmet 200 includes one or more of the following: an accelerometer 202, a mouthguard 204, a memory 206, a gyroscope 208, a processor 210, a transceiver 212, and a power supply 214. In exemplary embodiments, the power supply 214 may be a battery configured to provide power to one or more of the accelerometer 202, the memory 206, the gyroscope 208, the processor 210, and the transceiver 212.

In one embodiment, the mouthguard 204 is attached to the helmet 200 via a clip that provides communicative coupling between the mouthguard 204 and the processor 210 or the transceiver 212. The mouthguard 204 is configured to analyze biomarkers in the saliva of the user to detect a biomarker in the saliva that may indicate that the user has suffered a traumatic brain injury. Upon detecting such a biomarker, the mouthguard 204 transmits an alert to the processor 210 of the helmet 200. In exemplary embodiments, the processor 210 of the helmet 200 is configured to transmit an alert, via the transceiver 212, to a separate processing system in response to receiving the alert from the mouthguard 204.

In another embodiment, the mouthguard 204 is attached to the helmet 200 via a tube that provides fluid coupling between the mouthguard 204 and the lab on chip 216. The mouthguard 204 is configured to collect samples of saliva and to direct the samples to the lab on chip 216 in the helmet 200. In exemplary embodiments, the specimens of saliva are collected by mouthguard and are directed to the lab on chip 216 by active or passive suction. The lab on chip 216 is configured to analyze biomarkers in the saliva of the user to detect a biomarker in the saliva that may indicate that the user has suffered a traumatic brain injury. Upon detecting such a biomarker, the lab on chip 216 transmits an alert to the processor 210. In exemplary embodiments, the processor 210 of the helmet 210 is configured to transmit an alert, via the transceiver 212, to a separate processing system in response to receiving the alert from the lab on chip 216. In exemplary embodiments, the lab on chip 216 may utilize microfluidics, onboard chemistry analysis, and nanoscale sequencing array technology to analyze the saliva for biomarkers.

In one embodiment, the processor 210 is configured to receive an output from one or more of the accelerometer 202 and the gyroscope 208 and store data in memory 206 about impacts experienced by helmet 200. In exemplary embodiments, the processor 210 is configured to monitor data received from the accelerometer 202 and the gyroscope 208 and to transmit an alert if the data received indicates that the helmet 200 has suffered a severe impact. As used herein, the term severe impact is an impact sufficient to cause a traumatic brain injury. The processor 210 may compare the data received from the accelerometer 202 and the gyroscope to one or more threshold values for determining if an impact experienced by the helmet 200 is severe. In exemplary embodiments, the processor 210 may stores all of the data received from the accelerometer 202 and the gyroscope 208 in the memory 206.

Figure 3:
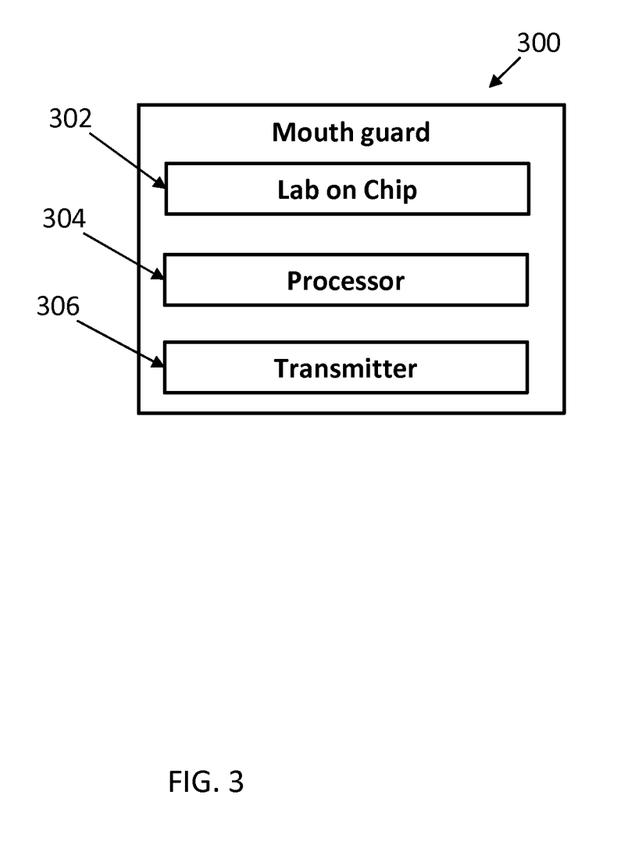
FIG. 3 is a block diagram illustrating a mouthguard in accordance with an exemplary embodiment.

Referring to FIG. 3, a block diagram illustrating a mouthguard 300 in accordance with an exemplary embodiment is shown. As illustrated the mouthguard 300 includes a lab on chip 302, a processor 304 and a transmitter 306. The lab on chip 302 is configured to analyze biomarkers in the saliva of the user to detect a biomarker in the saliva that may indicate that the user has suffered a traumatic brain injury. In exemplary embodiments, the lab on chip 302 may utilize microfluidics, onboard chemistry analysis, and nanoscale sequencing array technology to analyze the saliva for biomarkers. In exemplary embodiments, the processor 304 may monitor the output of the lab on chip 302 and may transmit an alert via the transmitter 306 when the lab on chip 302 detects a biomarker that indicates that the user has suffered a traumatic brain injury. In exemplary embodiments, the lab on chip 302, a processor 304 and a transmitter 306 may be disposed on a single chip or may be disposed on discrete chips.

In one embodiment, the lab on chip, whether disposed in the helmet or in the mouthguard, may be configured to continually test the saliva of the user as the mouthguard is in use. In another embodiment, the lab on chip, whether disposed in the helmet or in the mouthguard, may be configured to selectively test the saliva of the user when directed to do so by the processor of the helmet. For example, the helmet may utilize the sensors in the helmet to detect an impact to the user and if the impact exceeds a threshold level, the processor of the helmet may instruct the lab on chip to test the saliva for one or more biomarkers. In exemplary embodiments, the processor may intentionally interpose a delay between the detected impact that the execution of a test on the saliva by the lab on chip. The delay may allow time for the chemistry of the saliva to change as a result of the impact. In exemplary embodiments, the length of the delay may be determined based on the severity of the impact experienced and/or based on the medical history of the user.

In exemplary embodiments, the processor of the helmet may be configured to receive a medical history of the user from a separate processing system, which can be utilized in determining if an impact experienced by the helmet is a severe impact. For example, a user that has suffered multiple concussions may be more sensitive to impacts than users that have not previously suffered a concussion. As a result, the processor may utilize different functions for determining if an impact experienced by the helmet is a severe impact based on the medical history of the user.

Figure 4:
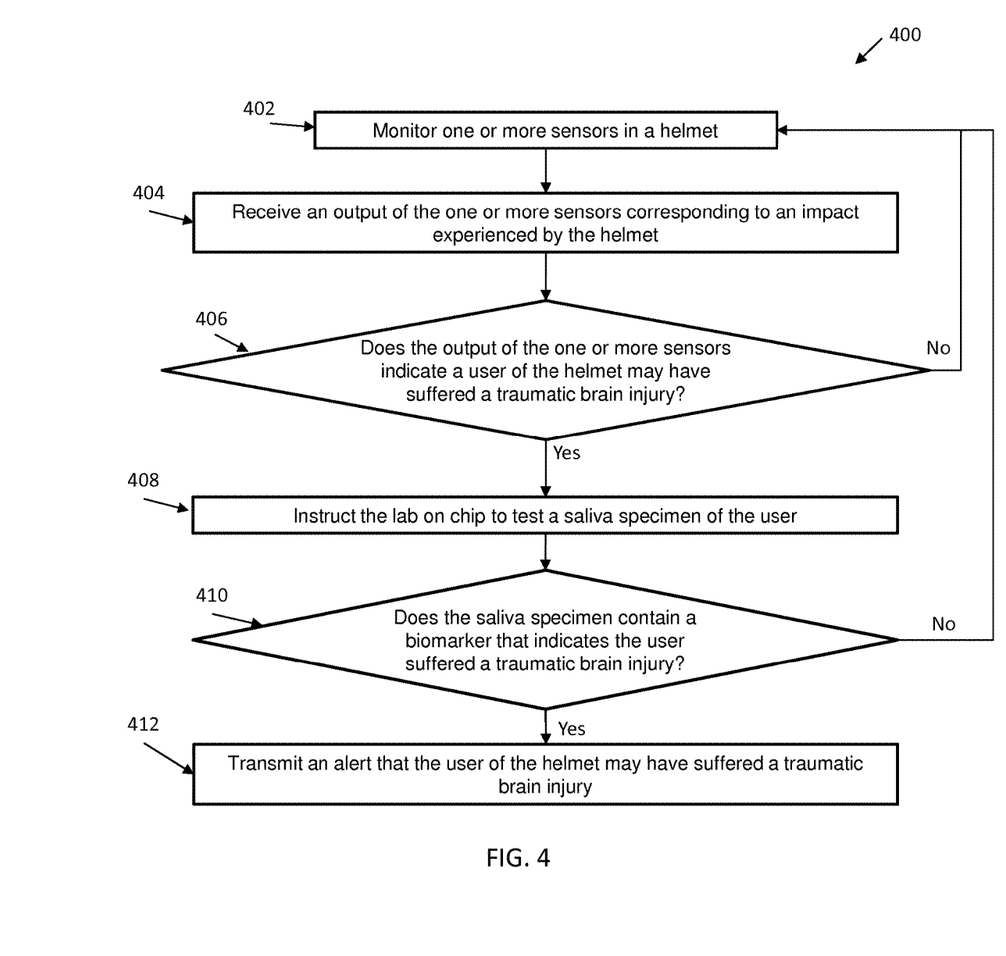
FIG. 4 is a flow diagram of a method for monitoring a user for a traumatic brain injury in accordance with an exemplary embodiment.

Referring now to FIG. 4, a flow diagram of a method 400 for monitoring a user for a traumatic brain injury in accordance with an exemplary embodiment is shown. As shown at block 402, the method 400 includes monitoring one or more sensors in a helmet. In exemplary embodiments, the one or more sensors include an accelerometer and a gyroscope. Next, as shown at block 404, the method 400 includes receiving an output of the one or more sensors corresponding to an impact experienced by the helmet. As shown at decision block 406, the method 400 includes determining if the output of the plurality of sensors indicates a user of the helmet may have suffered a traumatic brain injury. In exemplary embodiments, determining if the output of the plurality of sensors indicates a user of the helmet may have suffered a traumatic brain injury may include comparing the output of the plurality of sensors to one or more stored profiles corresponding to normal measurements from each of the plurality of sensors or to one or more thresholds for each of the plurality of sensors. If the output of the plurality of sensors indicates that the user of the helmet may have suffered a traumatic brain injury, the method 400 proceeds to block 408 and includes instructing a lab on chip to test a saliva specimen of the user. In exemplary embodiments, the lab on chip may be disposed in a mouthguard in communication with the helmet or with the helmet. If the output of the plurality of sensors indicates that the user of the helmet has not suffered a traumatic brain injury, the method 400 returns to block 402 and continues to monitor the output of the plurality of sensors.

Continuing with reference to FIG. 4, as shown at decision block 410, the method 400 includes determining if the saliva specimen contains a biomarker that indicates the user suffered a traumatic brain injury. If the saliva specimen does not contain a biomarker that indicates the user suffered a traumatic brain injury, the method 400 returns to block 402 and continues to monitor the output of the plurality of sensors. Otherwise, the method 400 proceeds to block 412 and includes transmitting an alert that the user of the helmet may have suffered a traumatic brain injury. In exemplary embodiments, the alert transmitted by the helmet that the user of the helmet may have suffered a traumatic brain injury may include, but is not limited to, one or more of: an identification of the user; the identification of the biomarker detected in the saliva; a concentration of the biomarker detected in the saliva; data regarding any impacts experienced by the user in a predefined time period prior to the transmission; and an indication of a confidence level associated with indication that the user may have suffered a traumatic brain injury.

Figure 5:
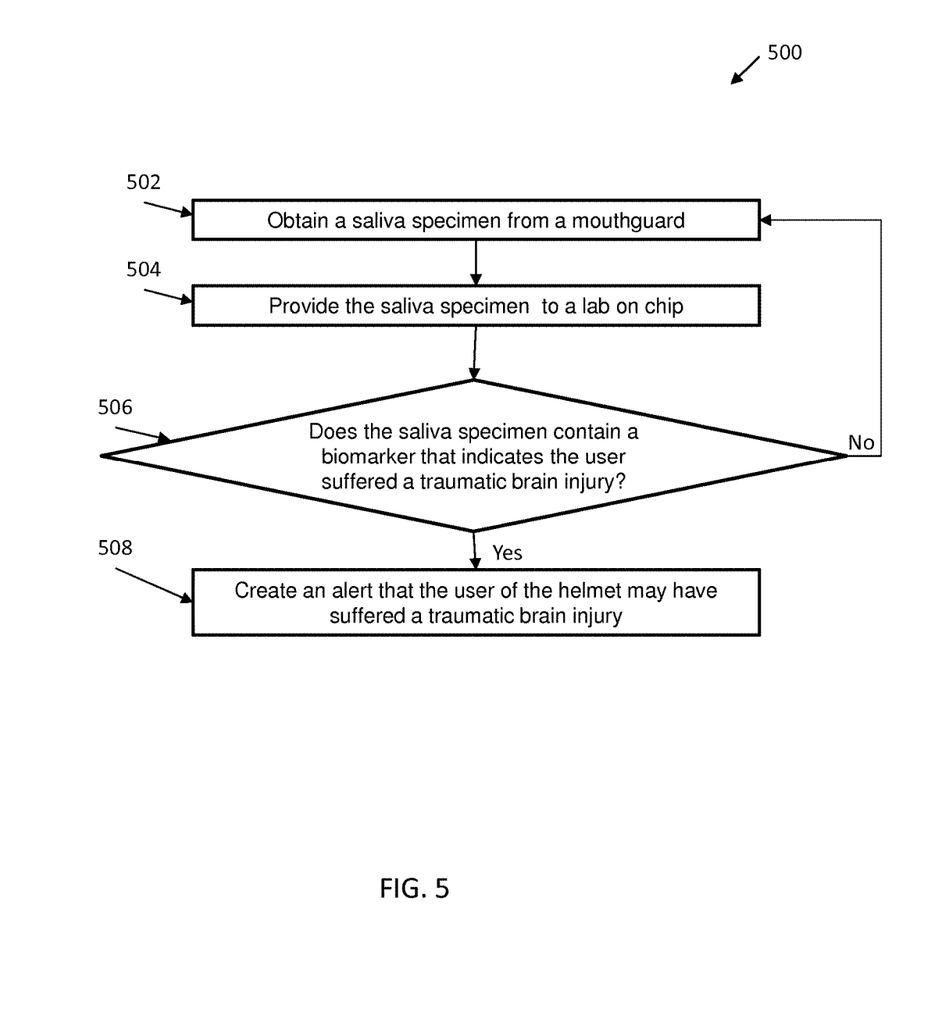
FIG. 5 is a flow diagram of another method for monitoring a user for a traumatic brain injury in accordance with an exemplary embodiment.

Referring now to FIG. 5, a flow diagram of another method 500 for monitoring a user for a traumatic brain injury in accordance with an exemplary embodiment is shown. As shown at block 502, the method 500 includes obtaining a saliva specimen from a mouthguard. Next, as shown at block 504, the method 500 includes providing the saliva specimen to a lab on chip. In exemplary embodiments, the lab on chip may be disposed within the mouthguard or it may be disposed within a helmet in fluid communication with the mouthguard. As shown at decision block 506, the method 500 includes determining whether the saliva specimen contains a biomarker that indicates the user suffered a traumatic brain injury. If the saliva specimen contains a biomarker that indicates the user suffered a traumatic brain injury, the method proceeds to block 508 and includes creating an alert that the user of the helmet may have suffered a traumatic brain injury. Otherwise, the method 500 returns to block 502 and obtains a new saliva specimen from the mouthguard. In exemplary embodiments, the method 500 may be configured to execute periodically, i.e., a new saliva specimen may obtained and tested every five, ten, etc. minutes while the mouthguard is in use.

Figure 6:
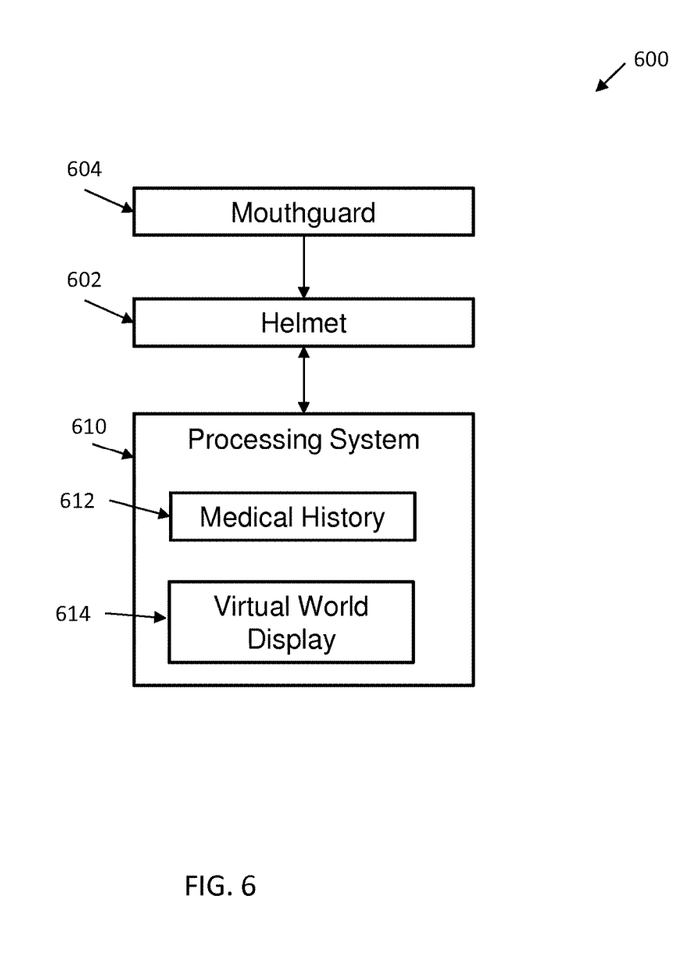
FIG. 6 is a block diagram illustrating a system for monitoring helmets in accordance with an exemplary embodiment.

Referring now to FIG. 6, a block diagram illustrating a system 600 for monitoring users of helmets for traumatic brain injuries in accordance with an exemplary embodiment is shown. As illustrated the system 600 includes a helmet 602, such as the one shown and described above with reference to FIG. 2, a processing system 610, such as the one shown and described above with reference to FIG. 1, and a mouthguard 604, such as the one shown and described above with reference to FIG. 3. The processing system 610 is configured to communicate with the helmet 604 and is also configured to store the medical history 612 of the users of the helmets 602. In exemplary embodiments, the medical history 612 of the users of the helmets 602 may be used by the helmet 602 in determining a threshold level for a severe impact. In addition, the medical history 602 may be used during the analysis of saliva by the lab on chip, which may be disposed in the helmet 602 or the mouthguard 604. In exemplary embodiments, the processing system 610 may include a virtual world display 614 that is configured to provide a display a real-time status of each of the users of the helmets. In exemplary embodiments, the status may include indications that the user may have suffered a traumatic brain injury, duration of play of the user, a duration that the user has been in the current category of play, or the like.

In exemplary embodiments, the user's history of collision or medical concerns may be used to determine a traumatic brain injury risk assessment, either by the embedded processor or the separate processing system. In addition, the helmet may be configured to provide a real-time feed of the user's cognitive state to increase the confidence level of the need for a particular alert or indication. In exemplary embodiments, an aggregate indication may be used to summarize an overall state of a group of players. This may also help to potentially identify area of risk in the dynamics of player-player interaction, overly aggressive players, playing field conditions, etc. In exemplary embodiments, an automatic feed from a user's history of collision or medical concerns may also be provided to a processor of the helmet in order to update an impact risk model for each category of play. In addition, the processing system 610 may receive a real-time feed of the user's cognitive state, which can be used to update the risk models used by the helmets. The risk models may also be sent to the virtual world display 614 of the game and players, which allows the sports staff health professionals to visualize the nature of potential problems.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for monitoring a user for traumatic brain injuries, the method comprising:
   determining that the user has suffered a severe impact;
   obtaining a saliva specimen from a mouthguard that is worn by the user, wherein obtaining the saliva specimen from the mouthguard is performed after a delay period from the severe impact, wherein the delay is determined based on a severity of the severe impact experienced by the user;
   providing the saliva specimen to a lab on chip;
   analyzing the saliva specimen for one or more biomarkers; and
   creating an alert that the user of the mouthguard may have suffered a traumatic brain injury, wherein the alert includes an indication of the one or more biomarkers, a concentration of the one or more biomarkers and an identification of the user.

2. The method of claim 1, wherein the lab on chip is disposed within the mouthguard.

3. The method of claim 1, wherein the lab on chip is disposed within a helmet that is in fluid communication with the mouthguard.

4. The method of claim 1, wherein the determination that the user has suffered a severe impact is based on a determination that a helmet worn by the user has experienced an acceleration above a threshold amount.

5. The method of claim 4, wherein the threshold amount is based upon a medical history of the user.

6. The method of claim 1, wherein the delay is further determined based on a medical history of the user.

\* \* \* \* \*